US006183417B1

United States Patent
Geheb et al.

(10) Patent No.: US 6,183,417 B1
(45) Date of Patent: Feb. 6, 2001

(54) DOCKING STATION FOR A PATIENT MONITORING SYSTEM

(75) Inventors: Frederick J. Geheb, Danvers; Michael Maschke, Beverly, both of MA (US); Clifford Mark Kelly, Goffstown, NH (US)

(73) Assignee: Siemens Medical Systems, Inc., Iselin, NJ (US)

( * ) Notice: Under 35 U.S.C. 154(b), the term of this patent shall be extended for 0 days.

(21) Appl. No.: 08/401,332

(22) Filed: Mar. 9, 1995

Related U.S. Application Data

(63) Continuation of application No. 08/252,153, filed on Jun. 1, 1994, now abandoned, which is a continuation of application No. 07/989,410, filed on Dec. 11, 1992, now abandoned.

(51) Int. Cl.$^7$ .................................................... G06F 19/00
(52) U.S. Cl. ............................................................ 600/301
(58) Field of Search .................... 364/413.02, 403.03, 364/413.05, 413.06; 128/710; 600/300, 301

(56) References Cited

U.S. PATENT DOCUMENTS

| | | | |
|---|---|---|---|
| 3,940,742 | * 2/1976 | Hudspeth et al. | 364/413.03 |
| 4,121,574 | * 10/1978 | Lester | 128/666 |
| 4,325,385 | 4/1982 | Holte . | |
| 4,356,475 | 10/1982 | Neumann et al. . | |
| 4,378,021 | 3/1983 | Strand . | |
| 4,688,579 | 8/1987 | Inahara | 128/695 |
| 4,715,385 | 12/1987 | Cudahy et al. . | |
| 4,724,844 | 2/1988 | Rafelson . | |
| 4,814,759 | 3/1989 | Gombrich et al. . | |
| 4,835,372 | * 5/1989 | Gombrich et al. | 235/375 |
| 4,895,161 | 1/1990 | Cudahy et al. . | |

(List continued on next page.)

FOREIGN PATENT DOCUMENTS

| | | |
|---|---|---|
| 524992 | 8/1972 | (CH) . |
| 0261927 | 3/1988 | (EP) . |
| 0553372 | 8/1993 | (EP) . |
| WO81/02832 | 10/1981 | (WO) . |

OTHER PUBLICATIONS

Hewlett Packard brochure: "Patient Data Management System—System Description", Manual Part #78707–91998–9 Jan. 1982.
Marquette Electronics, Inc. brochure: Unity Monitoring Network—The Power of Integrated Patient Monitoring, 1990.
"Introduction to the HP Component Monitoring System", Christoph Westerteicher, Hewlett–Packard Journal 42 (1991) Oct., No. 4, Palo Alto, CA US, pp. 6–10.

Primary Examiner—D. McElheny, Jr.
(74) Attorney, Agent, or Firm—Mark H. Jay

(57) ABSTRACT

A docking station for a portable patient monitor is adapted for use in a system which includes a communications network and, optionally, a bedside display. The portable monitor is coupled to sensors for receiving patient data signals. The docking station includes a platform that can be conveniently located near the patient. The platform has a detachable mounting which holds the portable monitor. When the portable monitor is mounted on the docking station platform, it receives power from the docking station. At the same time, the docking station receives patient data from the portable monitor and transfers the data to the communications network. The docking station is also coupled, via the communications network, to a plurality of input and output devices when it is mounted on the docking station. A second example of the docking station includes a power supply and network (PSN) box that is mounted to a wall or other fixed surface. The docking station platform receives power and network services from the PSN box. The PSN box may be detached from the wall and attached directly to the monitor for semi-permanent installation of the monitor.

34 Claims, 6 Drawing Sheets

U.S. PATENT DOCUMENTS

| | | |
|---|---|---|
| 5,012,471 | 4/1991 | Policastro et al. . |
| 5,016,172 * | 5/1991 | Dessertine ........................ 364/413.02 |
| 5,019,974 * | 5/1991 | Beckers ........................... 364/413.02 |
| 5,024,225 | 6/1991 | Fang . |
| 5,025,374 * | 6/1991 | Roizen et al. ................... 364/413.02 |
| 5,025,808 | 6/1991 | Hafner . |
| 5,133,346 * | 7/1992 | Kulkarni .......................... 128/202.22 |
| 5,181,521 * | 1/1993 | Lemelson ............................ 128/736 |
| 5,191,891 * | 3/1993 | Righter ............................... 128/710 |

\* cited by examiner

DOCKING STATION FOR A PATIENT MONITORING SYSTEM

CROSS-REFERENCE TO RELATED APPLICATION

This is a continuation of Ser. No. 08/252,153 filed Jun. 1, 1994 now abandoned which is a continuation of Ser. No. 07/989,410 filed Dec. 11, 1992, now abandoned.

CROSS REFERENCE TO RELATED APPLICATIONS

The following U.S. applications which are assigned to the same assignee as the instant application and filed concurrently therewith have related subject matter:

U.S. Ser. No. 07/988,989, U.S. Pat. 5,375,604, entitled TRANSPORTABLE MODULAR PATIENT MONITOR; U.S. Ser. No. 07/989,414 entitled DATA ACQUISITION POD FOR A PATIENT MONITORING SYSTEM; 07/989,415 entitled TRANSPORTABLE MODULAR PATIENT MONITOR WITH DATA ACQUISITION MODULES; and U.S. Ser. No. 07/989,416 entitled PRESSURE DATA ACQUISITION DEVICE FOR A PATIENT MONITORING SYSTEM.

FIELD OF THE INVENTION

The present invention relates to medical systems and in particular to patient monitoring systems for collecting, storing transmitting and displaying medical data.

BACKGROUND OF THE INVENTION

In hospitals and other health care environments, it is often necessary to continually collect and analyze a variety of medical data from a patient. These data may include electrocardiogram, temperature, blood pressure, respiration, pulse and other parameters.

Monitoring systems in the related art have typically fallen into one of two general categories: multi-function monitoring, recording and displaying systems which process and collect all of the data desired, but are bulky and difficult to transport; and small, portable systems which are easy to transport, but process and collect fewer types of data and have limited storage capability. Initially (e.g., in an ambulance or an emergency room) a patient is connected to a simple, portable monitor to observe a limited number of medical attributes, such as EKG or non-invasive blood pressure. As the patient moves to higher care facilities (e.g., an intensive care unit or operating room) it is desirable to augment these simple monitors to observe additional parameters. Generally, this is accomplished by disconnecting the patient from the simple monitor and connecting the patient to a monitoring system having more robust capabilities.

The need for continuity of data collection and display is most pressing in emergency situations. During an emergency, the speed at which a patient is transferred from a bed to an operating room or intensive care unit may substantially impact the patient's chance of survival. It is important to provide the same level of monitoring in transport as at the stationary bedside. It is desirable from a clinical point of view to provide a continuous monitoring capability and data history availability which follow the patient.

Two major considerations in the design of transport monitoring systems have been ease and speed of system reconfiguration. It is undesirable to disconnect the patient from a set of sensors coupled to a fixed location monitoring system and attach a new set of sensors coupled to a portable monitor immediately prior to transportation or administration of critical procedures. It is equally undesirable to disconnect each sensor from a fixed location monitoring system and reconnect the individual sensors to a portable monitoring system for transport.

U.S. Pat. Nos. 4,715,385 and 4,895,385 to Cudahy et al. discuss a monitoring system which includes a fixed location display unit and a portable display unit. A digital acquisition and processing module (DAPM) receives data from sensors attached to the patient and provides the data to either or both of the fixed and portable display units. Normally, the DAPM is inserted into a bedside display unit located near the patient's bed. When it is necessary to reconfigure the system for transporting the patient, the DAPM is connected to the portable display and then disconnected from the bedside display. The DAPM remains attached to the patient during this reconfiguration step and during patient transport, eliminating the need to reconnect the patient to intrusive devices. Once the DAPM is disconnected from the bedside display, a transportable, monitoring system is formed, comprising the portable display and DAPM.

A feature of the DAPM which may be undesirable is the need to connect cables between the DAPM and the transportable monitor to provide continuous monitoring during transport. In a life threatening situation, any time spent performing equipment configuring steps (such as connecting cables) to prepare the monitoring system for transport may impact the patient's chance for survival.

Another feature of the DAPM which may be undesirable is the need to have at least two displays (a portable monitor and a fixed display) if both portable operations and coupling to room related services are desired. The DAPM is connected to the patient to receive data. It is connected to the portable monitor during transport of the patient. In order to couple the patient data source to a power source or electronics in the patient's room or to a communications network, the DAPM must be inserted into the fixed display for coupling with any equipment fixed in the room (e.g., a hardcopy output device or an outside network. If there is no fixed display or if the fixed display is already in use, the DAPM cannot be connected to an external network. The configuration (portable display and DAPM) used while transporting the patient cannot connect directly to room related services.

Additional simplification of the steps performed to reconfigure the system is desirable, in order to reduce the time to prepare the patient and monitoring system for transport to an operating room or intensive care unit.

SUMMARY OF THE INVENTION

A docking station for a portable monitor is adapted for use in a system which includes a portable monitor and a communications network. The portable monitor displays and processes patient data signals from a plurality of sensors.

The docking station includes a detachable mounting which holds the portable monitor on the docking station. The portable monitor, when it is mounted on the docking station, provides patient data signals. The docking station transfers patient data to the communications network which is coupled to the docking station.

When the portable monitor is mounted on the docking station, the docking station provides power to the portable monitor as well as links to data from a plurality of communications networks and devices.

BRIEF DESCRIPTION OF THE DRAWINGS

FIG. 1b is an isometric view of the docking station and patient monitor shown in FIG. 1a.

FIG. 2 is an isometric view of the docking station shown in FIG. 1a.

FIG. 3 is a front view of apparatus suitable for use as the wall box shown in FIG. 1a.

FIG. 4 is a isometric view of a second exemplary embodiment of the wallbox shown in FIG. 1a.

DETAILED DESCRIPTION OF THE EXEMPLARY EMBODIMENTS

Figure 1A:
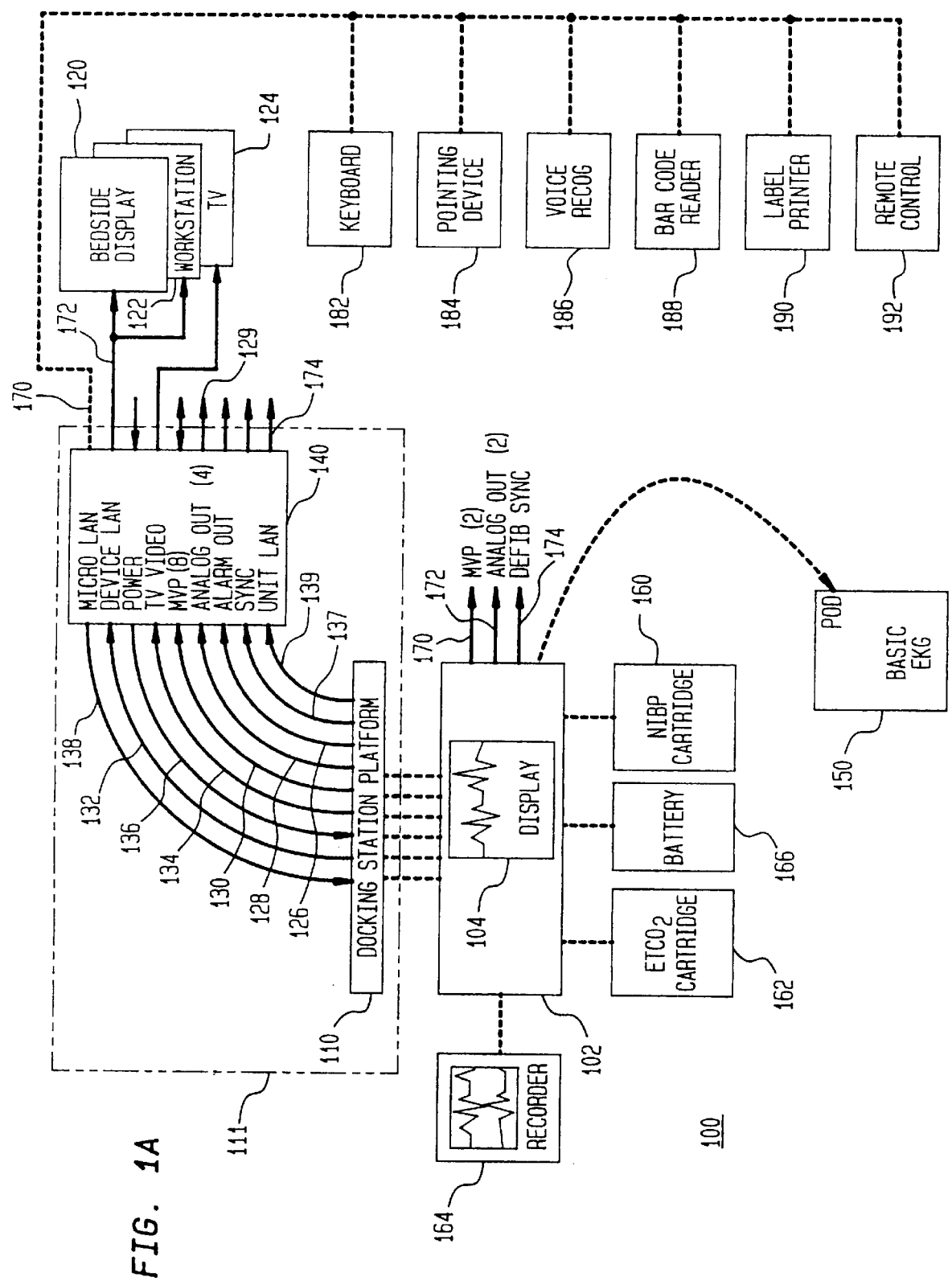
FIG. 1a is a block diagram of a system which includes a docking station in accordance with the invention.

An exemplary docking station system 100 including a docking station 111 in accordance with the present invention is shown in FIG. 1a. A portable monitor 102 acquires physiological data signals from a plurality of sensors (not shown), which may include both invasive and non-invasive devices for collecting physiological data from a patient. The portable monitor 102 displays the physiological data, and transmits patient data signals to docking station 111 (It will be understood by one skilled in the art that the term "patient data", as used herein, may refer to the processed information derived from the signals produced by sensors attached to the patient. Thus "patient data" in this sense may include, for example, red, green and blue raster-scan video signals toldrive a slave display, or signals to provide status and control information to control auxiliary devices). The docking station 111 provides power and communications services to the portable monitor 102 while monitor 102 is mounted on the docking station. The mounting mechanism provides for rapid disconnection of the monitor 102 from the docking station 111 (both mechanically and electrically) for transport. Preferably, the disconnection is accomplished in a single step, so that the user can pick up monitor 102 and transport it to another location, without handling any individual cables or connectors.

In the first exemplary embodiment, docking station 111 includes two modular components. The first component is the docking station platform 110. Portable monitor 102 may be placed on the docking station platform 110, which may be positioned in the patient area, for example, near the patient's bed or attached to the bedframe. Docking station platform 110 provides mechanical support for the portable monitor 102, as well as connections to bedside display 120, power 134, and video display 124. Docking Station 111 can also communicate with local area networks (LANs) via couplings 170, 172 and 174. Docking station may provide communications with a computer or intelligent workstation 122, via the networks. Docking station 111 provides a simple mechanism to connect portable monitor 102 with several devices and networks without the need to connect individual cables for each device or network. Data and power connectors on the docking station platform 110 and on the case of portable monitor 102 allow simultaneous physical and electrical couplings to be established.

Figure 2:
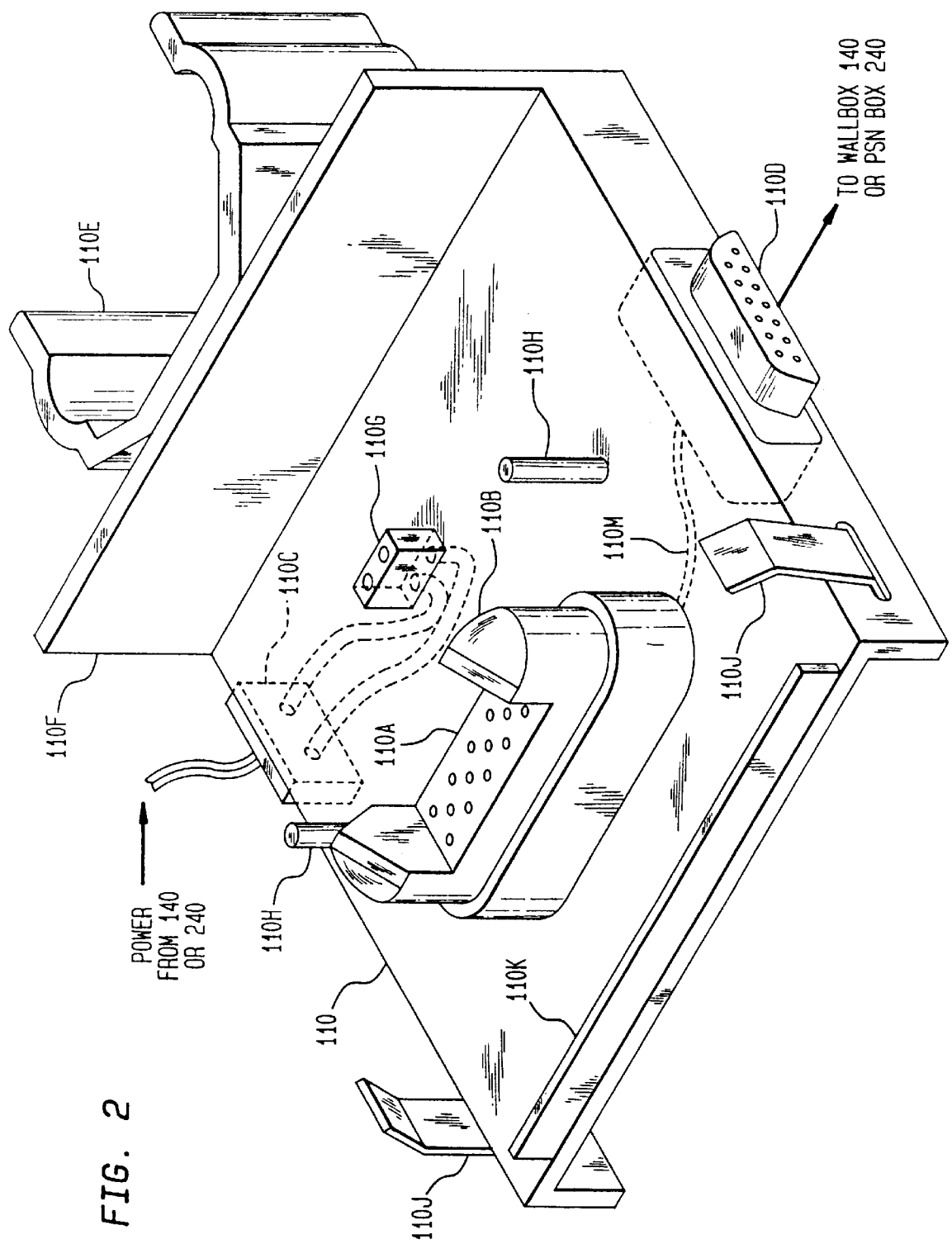

The second component is a power supply and network box 140 referred to herein as wallbox 140. Wallbox 140 is mounted to a wall or other stationary surface. Docking station 111 may, include a wallbox 140 coupled to connectors 110c and 110d as shown in FIG. 2. The wallbox 140 provides power for operating monitor 102 and for charging a battery pack within (or attached to) monitor 102. Wallbox 140 also provides communications links to networks and devices, both inside and outside of the room in which docking station 111 is located.

Portable monitor 102 is a self-contained, standalone monitoring system. Monitor 102 includes all of the processing electronics necessary to process, display and store patient data during transport. In the exemplary embodiment described herein, portable monitor 102 does not include a broad suite of network interfaces; during transport, the exemplary monitor 102 does not have any connections to a central monitoring system or to communications networks. Portable monitor 102 has a rechargeable battery pack for use during transport. Portable monitor is also capable of receiving power from an external power supply. In the first exemplary embodiment of the invention, power is received from wallbox 140 by way of docking station platform 110. In a second exemplary embodiment (described below with reference to FIGS. 4 and 5), portable monitor may receive power by either one of two different external methods: (1) via docking station platform 110, and (2) via a Power Source and Network (PSN) box 240 that attaches directly to monitor 102.

The bedside display 120 may be a slave unit receiving signals for display from docking station 111. Alternately, bedside display 120 may be a conventional bedside patient monitoring unit which receives, stores, processes, displays and transmits medical data. Alternately, the bedside display may be an intelligent workstation 122 with a VGA display and conventional disk storage.

Figure 1B:
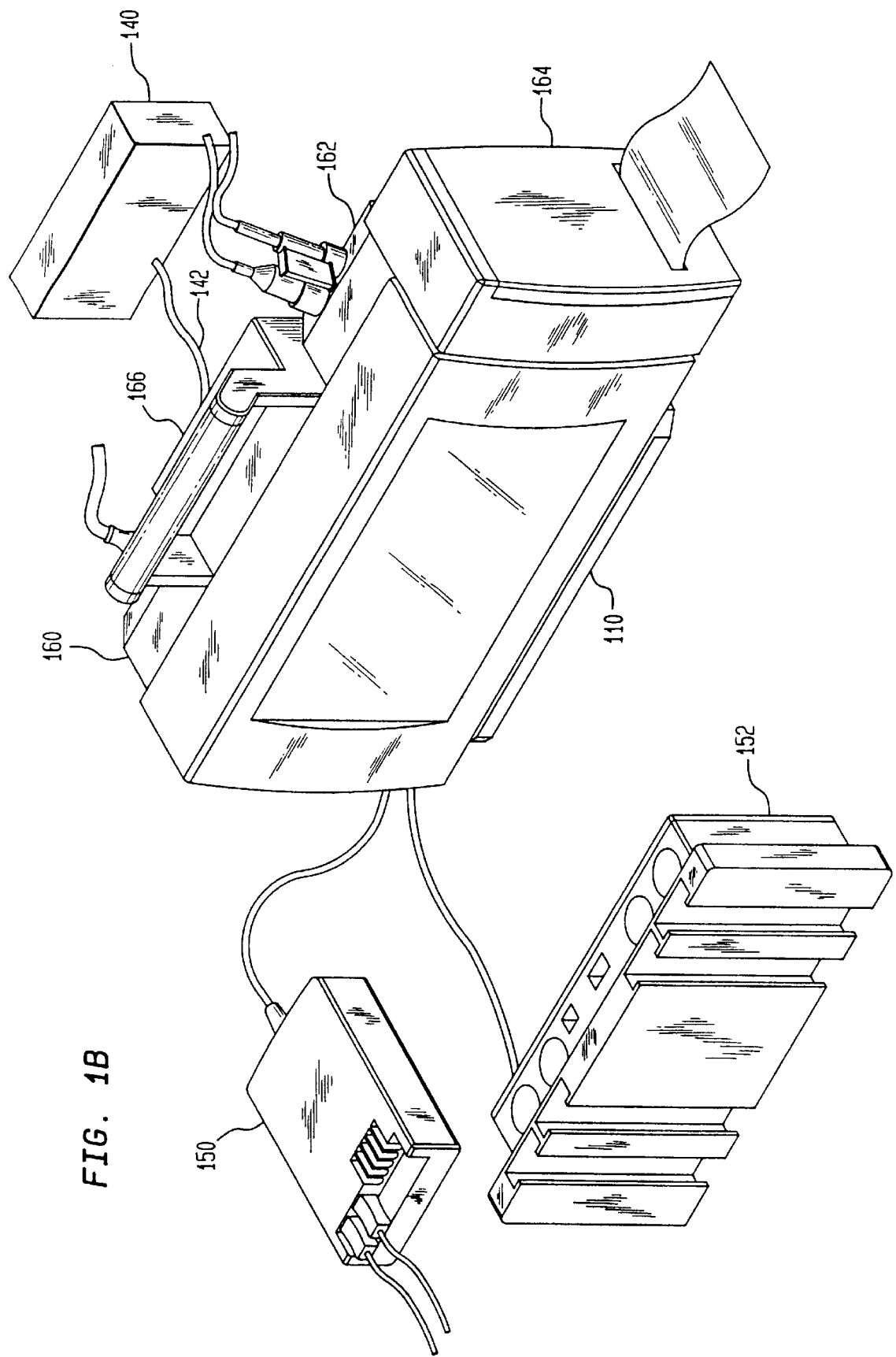

FIG. 1b shows an isometric view of the first exemplary embodiment of the invention, including a docking station platform 110, a wallbox 140 and monitor assembly 100 of FIG. 1a. The docking station platform 110 is connected to wallbox 140 by one or more cables 142. Portable monitor 102 is mounted on docking station platform 110, providing physical support, power, and communications. Monitor 102 acquires physiological data signals from data acquisition pods 150 and 152 for EKG data for pressure data, respectively. A non-invasive blood pressure cartridge 160 and an end tidal $CO_2$ cartridge 162 collect additional patient data. Cartridges 160 and 162, a hardcopy recorder 164 and a battery pack 166 are individually attached to portable monitor 102 for purposes of illustration.

FIG. 2 shows an isometric view of an exemplary docking station platform 110 to which portable monitor 102 may be attached. A connector 110a provides data communications couplings to the portable monitor. A guide 110b, which may be integral with connector 110a as shown in FIG. 2, facilitates proper positioning of monitor 102 on docking station platform 110, and assists in maintaining monitor 102 in position while monitor 102 is on docking station platform 110. Guide 110b prevents sideways motion between the portable monitor and the docking station. Optional guide pins 110h and vertical member 110k may be used in addition to, or in place of, guide 110b to assist in positioning the portable monitor 102 and preventing horizontal motion when monitor 102 is mounted on docking station platform 110.

A plurality of latches 110j are shown pivotably mounted to the sides of docking station platform 110. The latches 110j may be attached to the portable monitor 102 to prevent vertical motion so the portable monitor cannot be accidentally lifted off while mounted to the docking station. It is understood by those skilled in the art that a variety of conventional detachable fasteners may be substituted for latches 110j.

Many variations of the docking station mechanical configuration are possible. For example, connector 110a and guide 110b may be separate from one another. There may be multiple connectors 110a to transmit data between portable monitor 102 and docking station 111. Additional mechanical fasteners may be added to improve the stability of the detachable mounting.

Figure 3:
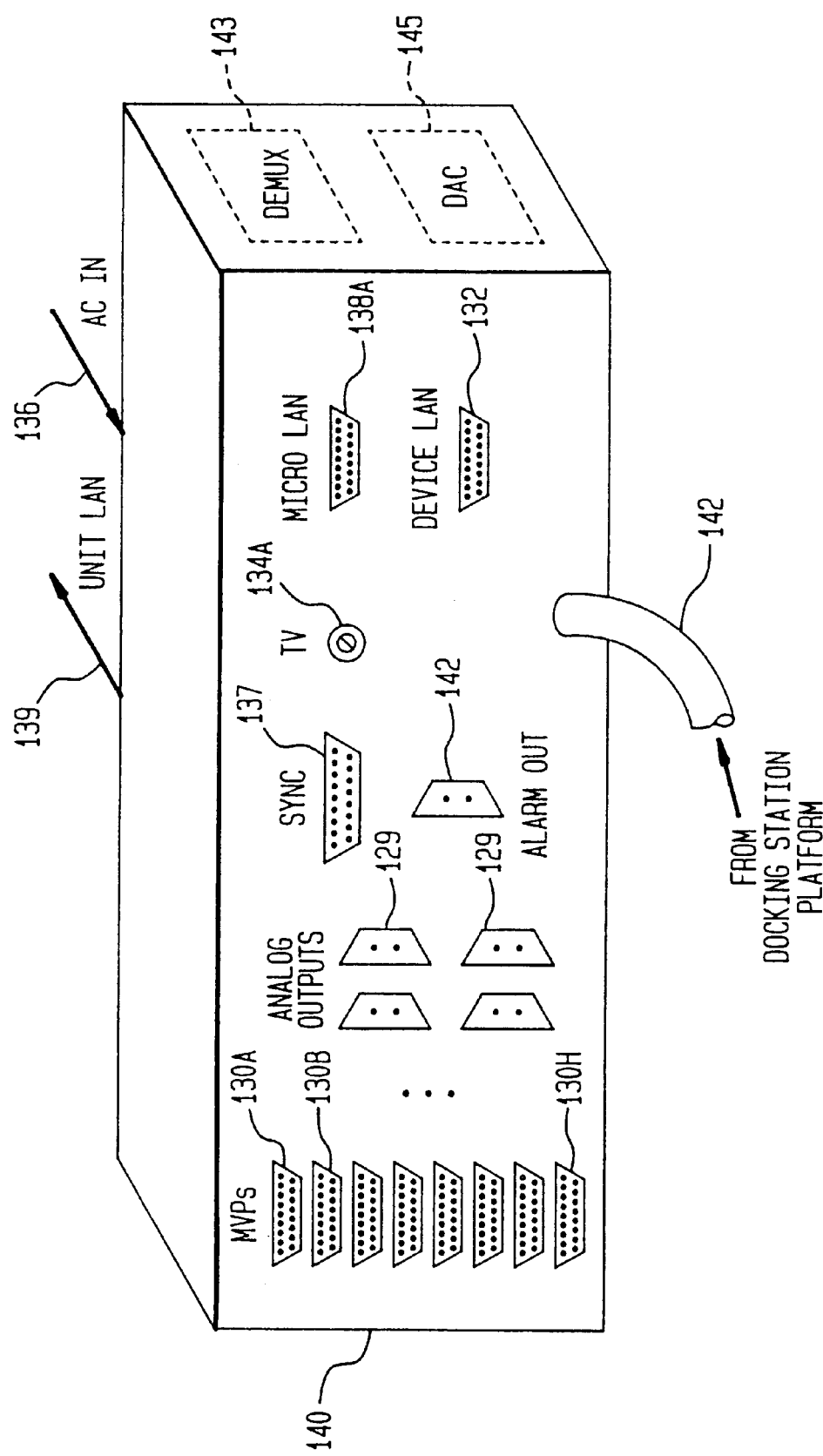

An optional clamp 110e may be used to mount docking station 111 in a variety of locations, including but not limited to: on an intravenous (IV) pole (not shown), a shelf or a bed frame. When mounting the docking station platform 110 to a bed or IV pole, both of which are movable, it is desirable to provide a fixed junction box 140 (also referred to as a wallbox) for coupling the docking station with power, devices and networks outside of the room in which the docking station is located. A wallbox 140 suitable for this purpose is shown in FIG. 3. Alternatively, clamp 110e may be omitted and backplate 110f may be fastened directly to the wallbox 140.

Referring to FIG. 2, a separate connector llog provides power to the portable monitor 102. Connector 110d provides data communications links from portable monitor 102 to external devices and networks, when monitor 102 is on docking station platform 110. Connector 110b may be a conventional connector which interfaces directly to a local area network (LAN). The network may use one of a variety of known LAN protocols, such as carrier sense multiple access with collision detection (CSMA/CD). Additionally, the data may be output to a conventional patient monitoring system bedside display 120 and/or to a customized intelligent workstation 122. Docking station 111 electrically isolates electrical paths connected to the portable monitor 102.

Docking station 111 provides 12 volt DC power to the portable monitor 102 via connector 110c and 110g, for operating the monitor when it is mounted on the docking station platform 110. Portable monitor 102 includes a battery charger and a nickel-cadmium battery 166 (shown in FIG. 1a). The battery charger includes connectors and a switch to provide charge to the battery. The docking station 111 transmits a signal to the battery charger to activate the switch, so that the battery charger recharges battery 166 while the portable monitor 102 is mounted on the docking station.

The portable monitor 102 includes alarm processing for the parameters monitored. The portable monitor 102 provides an alarm signal to the docking station 111 if any of these alarm conditions is present. The docking station 111 includes a separate line within cable 110m for receiving alarm signals, if these signals are generated by the portable monitor while it is mounted on the docking station. An alarm output signal is received by docking station platform 110 and transmitted via line 126 to the wallbox 140 for closing relays to activate local alarm devices, such as a light or siren.

The docking station 111 also receives from the portable monitor 102 a synchronization signal which may be used to trigger a defibrillator. This signal is output from the wallbox 140.

Referring to FIG. 3, the wallbox 140 couples the docking station platform 110 to communications links which may include a plurality of local area networks (LANs) or bit serial or parallel-bit data links. The wallbox 140 includes buffer amplifiers to condition the docking station output signals for transmission over these LANs. In the exemplary embodiment, the wallbox 140 includes a conventional interface card (not shown) which converts the twisted pair CSMA/CD signal from line 139 (shown in FIG. 1a) to 10 Mbits/second signal suitable for transmission on a Thinnet LAN 174 (referred to as the Unit LAN) operating in accordance with the IEEE 802.3 Type 10-Base-2 standard. This Unit LAN 174 connects portable monitor 102 and bedside display 120 with remote stations for transferring patient data. The remote stations may be patient monitoring systems or computers. This Unit LAN 174 is configured to produce message delays of less than 2 seconds. It is understood by one skilled in the art that a different LAN protocol may be used for Unit LAN 174.

In the exemplary embodiment, wallbox 140 provides a direct video connection to a bedside display 120 using a protocol such as the Electronics Industries Association's RS-232-C Interface Standard. When the portable monitor 102 is on the docking station platform 110, monitor 102 drives bedside display 120, using the RS-232-C link. Alternatively, wallbox 140 may include a second conventional interface card (not shown) for interfacing a second LAN 172 (referred to as the Device LAN), which may, for example, be a 10 Mbit/sec. CSMA/CD LAN, to the wallbox 140. The Device LAN is used within a patient's room or operating room, or to distribute patient data via a central station. The Device LAN provides the main communications path to transfer patient data from the portable monitor 102 to a bedside display 120 within the same room in near real-time. This LAN is configured to maintain short delays and to allow a nominal 200 msec. response time between devices.

Wallbox 140 includes a third interface card (not shown) and a separate connection 138 which provides a coupling to an additional LAN for connecting input and output devices. This additional LAN may use a protocol such as High Level Datalink Control (HDLC) with device polling, for predictable response time. This additional LAN is referred to as the Micro LAN 170. The Micro LAN is used to connect input and output devices to the portable monitor 102 by way of the docking station 111. These devices (shown in FIG. 1a) may include keyboards 182, pointing devices 184, voice recognition 186 device, a bar code reader 188, a label printer 190, and a remote control 192. The remote control 192 may be either wired or infrared (IR). The wired remote control may be more desirable in an operating room (OR) environment, because the OR lights may distort IR control signals.

Although the exemplary embodiment, as shown in FIG. 3, includes three distinct LANs for connecting the docking station to remote stations, to local stations (i.e., those within the same room) and to I/O devices, it is understood by those skilled in the field of data communications that a variety of network configurations may be used to achieve a desired level of performance and reliability for these different types of traffic. In addition, the network configuration may be tailored to protect patients by isolating a device or class of devices on a separate LAN to prevent accidental or unauthorized use. Smaller installations may implement a single local area network within a site to accommodate all of the patient monitoring traffic.

Eight additional multivendor ports (MVP) 130 are provided to connect serial devices to the portable monitor and remote stations on the network using a known communications interface, e.g., the RS-232 interface standard.

Wall box 140 includes a demultiplexer 143 and a D/A converter (DAC) 145 which receives digital data from the portable monitor 102 and generates a plurality of analog waveform signals from the digital data. The analog signals are sent to port 129. Four analog output ports provide waveform data for transmission to external devices (e.g., displays, recorders). Thus, existing analog equipment may be connected to the portable monitor (which provides patient data in digital form in the exemplary embodiment) in order to display data collected by the monitor. By demultiplexing inside the wallbox 140 (as opposed to within the portable monitor 102 or the docking station platform 110), the electrical couplings between monitor 102 and docking station platform 110, and between docking station platform 110 and wallbox 140 are simplified.

Figure 4:
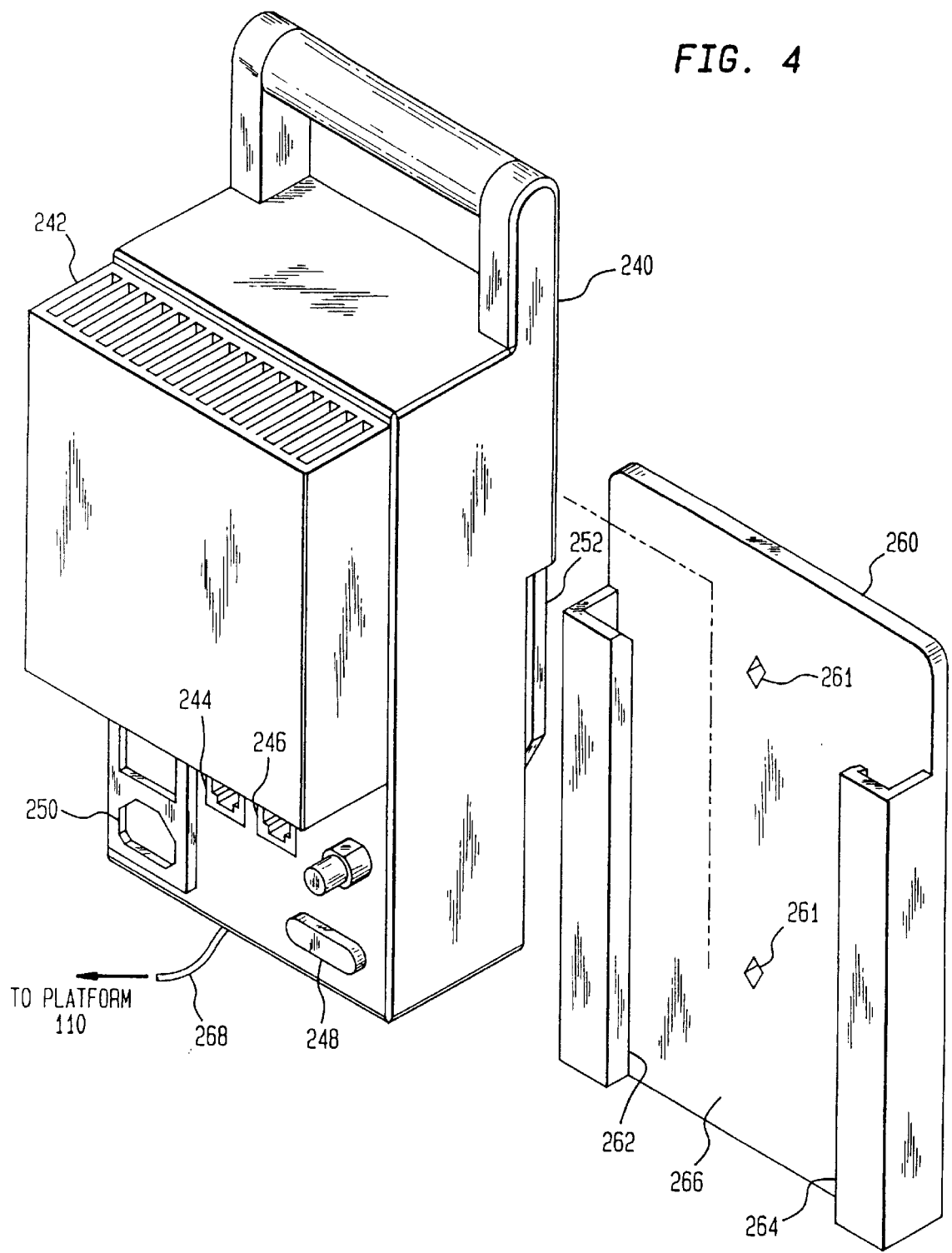
Figure 5:
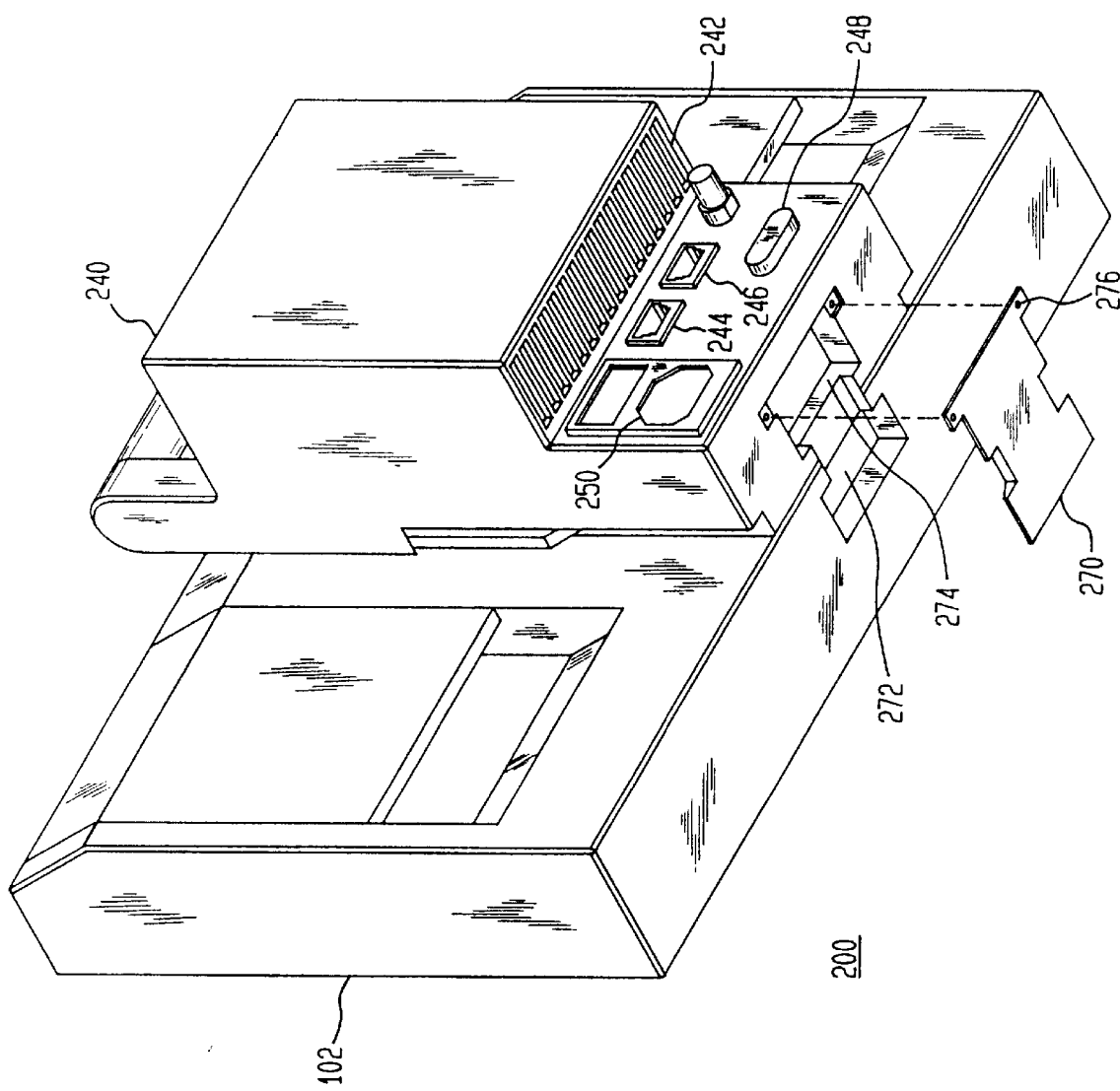
FIG. 5 is a rear isometric view of the wallbox shown in FIG. 4 attached to the monitor shown in FIG. 1.

FIGS. 4 and 5 show a second exemplary embodiment of the docking station power supply and network (PSN) box 240. Whereas wallbox 140, as shown in FIG. 3, is mechanically configured to be permanently mounted on a wall, PSN box 240 supports operation of monitor 102 in either one of two different configurations, shown in respective FIGS. 4 and 5.

In the configuration shown in FIG. 4, the PSN box 240 takes over part of the functionality provided by the docking station 111 (i.e., the functionality of the wallbox 140). In the configuration shown in FIG. 5, the PSN box 240 completely replaces the docking station 111; i.e., there is no docking station platform 110.

FIG. 4 shows a PSN box 240 in a configuration similar to that shown in FIG. 1a. PSN box 240 detachably mounts to the wall, bed or some other support on a bracket 260. In the exemplary embodiment, a plate 252 on the back of PSN box 240 slides down into a channel 266 formed between grooves 262 and 264 of bracket 260. PSN box 240 includes a plurality of connectors 244, 246, 248, and 250 for receiving respective cables (not shown). The cables couple the PSN box 240 to networks and to power, as described above with reference to wallbox 140 as shown in FIG. 3. Connector 250 receives AC power from the room. Connectors 244 and 246 connect PSN Box 240 to the micro LAN 170 (shown in FIG. 1a) and the Unit LAN 174 (shown in FIG. 1a), respectively. A serial port 248 provides an RS-232 link to a bedside display 120 (also shown in FIG. 1a).

In this configuration, the PSN box 240 is coupled to the portable monitor 102 via a cable 268 which connects the PSN box 240 to the docking station platform 110. This cable conveys the signals on the connectors 126 through 139 shown in FIG. 1a.

Although the exemplary PSN box 240 shown in FIG. 4 does not have as many ports as the wallbox 140 shown in FIG. 3, it is understood by one skilled in the art that a PSN box may be configured with the same number and types of ports as wallbox 140. Internally, PSN box may include the same configuration of network interface cards and electronics as wall box 140. It is understood by one skilled in the art that PSN box 240 may be constructed with additional interfaces as desired, or the suite of interfaces may be reduced in scope for use in smaller installations, such as the exemplary PSN box 240.

The primary difference between wallbox 140 and PSN box 240 is the mechanical packaging. Additional port(s) 274 (shown in FIG. 5) are provided on the bottom of PSN box 240. One or more cables 268 are attached to port(s) 274 to couple PSN box 240 to docking station platform 110, as shown in FIG. 2. In the configuration shown in FIG. 4, PSN box 240 is a functional equivalent of wallbox 140. PSN box 240 also includes a mounting plate 252 for easy mounting on, and removal from, mounting bracket 260. As shown in FIG. 4, bracket 260 may be permanently attached to a wall or other permanent surface, using conventional fasteners driven through mounting holes 261. PSN box 241 also includes an enclosed chimney heat sink 242 on the box.

FIG. 5 shows the same PSN box 240 installed in a different system configuration. Instead of mounting PSN box 240 on the wall, the PSN box 240 is attached to the back of monitor 102, in a "semi-permanent" manner, as defined below. Preferably, the portable monitor 102 is adapted to receive a battery 166 (as shown in FIG. 1b), and monitor 102 has a mounting channel (not shown), similar to channel 266, for receiving the battery. Once the battery 166 is removed from portable monitor 102, PSN box 240 may be attached to portable monitor 102 using the battery mounting channel of the monitor. In this configuration, docking station 111 (as shown in FIG. 1a) consists of the PSN box 240, without docking station platform 110.

In an alternative embodiment of the PSN box (not shown), PSN box 240 includes a connector (not shown) on the back of plate 252 for supplying power to monitor 102 via its battery connections when PSN box 240 is attached to monitor 102. Preferably the battery 166 and monitor 102 (shown in FIG. 1b) are configured so that an electrical coupling between them is formed when the battery 166 is mounted on the monitor 102. This same coupling may be replicated on PSN box 240, so that attaching the PSN box 240 to monitor 102 forms an electrical coupling without attaching any cables.

As shown in FIG. 5, PSN box 240 is attached to monitor 102 in a "semi-permanent" manner. As defined herein, the term "semi-permanent" means that monitor 102 and PSN box 240 may remain attached indefinitely; and there is no predetermined limit on the amount of time required to detach monitor 102 from PSN box 240. Separating monitor 102 from PSN box 240 may take anywhere from several seconds to a few minutes. This amount of time may be unacceptable in an emergency, but does not generally present a problem for routine operations. Preferably, the semi-permanent attachment technique is used for a monitor 102 which is not allocated by the user as a transport monitor. The monitor 102 is used in the same fashion as a fixed location monitoring system. This semi-permanent attachment may be contrasted to the detachable mounting means on docking station platform 110. Monitor 102 may be removed from docking station platform 110 within seconds, which is especially advantageous for transport in an emergency situation.

When the PSN box 240 is attached directly to monitor 102, the docking station platform 110 is not used. The assembly 200 consisting of the monitor 102 and the PSN box 240 may be placed on a table, a stand, or other suitable surface. In this configuration, the combination 200 of the monitor 102 and PSN box 240 may be considered a tethered monitor 200, which may be moved subject to constraints due to the power cord (not shown) and data communications cables (not shown). Instead of connecting the monitor 102 to the platform 110 and connecting platform 110 to wallbox 140 by a cable 268 (as shown in FIG. 4), PSN box 240 may be connected directly to the monitor 102. A coupling device 270 provides circuit paths between the connectors 272 and 274 on the bottom of portable monitor 102 and the bottom of PSN box 240, respectively.

Preferably, coupling device 270 includes the same connectors 110a and 110g that are used on docking station platform 110, for the interface with connector 272. Electrically, coupling device 270 performs the same functions as cable 142 and connectors 110a and 110g, as shown in FIG. 2. In addition, coupling device 270 provides structural support to prevent accidental separation of PSN box 240 from monitor 102. The semi-permanent attachment is formed using fasteners 276 which may, for example, be screws. The additional mechanical support provided by coupling device 270 is important because the assembly 200 may be jostled around accidentally. Assembly 200 rests on a surface, and may not be firmly attached to any structure.

The use of PSN box 240 as shown in FIG. 5 provides advantageous flexibility. When PSN box 240 is coupled to monitor 102 as shown in FIG. 5, the resulting combination provides the same functionality as a conventional bedside display unit in a compact form; ports 244 and 246 for interfacing with communications networks 170 and 174 and a coupling 250 for receiving power are provided. The PSN box 240 provides the network interface capability that is typically desired in a fixed location monitoring system, and is typically absent in transportable monitoring systems in the prior art. A separate docking station platform 110 is not required, which may reduce costs. This type of configuration may be desirable if the user does not intend to use the monitor 102 for patient transport under emergency conditions. PSN box 240 essentially converts a reduced function monitoring system (i.e., a system without network interface capability) into a full function monitoring system with network interfaces.

As user needs change, it may be desirable to reallocate this relatively fixed monitor for use as a transportable monitor. Connector 270 is easily removed in a few minutes. Portable monitor 102 may now be mounted on, or removed from, docking station platform 110 in substantially less than a minute. Monitor 102 may now be used as a bedside monitor while mounted on docking station platform 110, and as a transport monitor when removed from platform 110. By adding the docking station platform 110 and cable 268, the user has transformed the semi-permanent attachment into a modular system, with the capability to pick up the monitor and transport it, substantially avoiding any delays to configure the apparatus for transport.

It is understood by one skilled in the art that many variations of the embodiments described herein are contemplated. While the invention has been described in terms of exemplary embodiments, it is contemplated that it may be practiced as outlined above with modifications within the spirit and scope of the appended claims.

What is claimed:

1. Docking station apparatus adapted for use in a continuous patient monitoring system wherein the patient may be located within a first patient monitoring area, or transported out of said first patient monitoring area and into a second patient monitoring area remote from said first patient monitoring area, said system including a portable monitor adapted for being battery powered and coupled to a plurality of sensors, said monitor including means for continuously receiving, processing and displaying in real-time, patient physiological data signals provided by the sensors irrespective of said patient being located within said first or said second patient monitoring areas or being transported therebetween, and a communications network having an interface connection which is located in a relatively fixed position within said first and said second patient monitoring areas, the docking station apparatus including first and second docking station platforms, one in each of said first and second patient monitoring areas, respectively, each docking station platform comprising:

(a) mounting means for detachably coupling the portable monitor to the docking station platform so as to provide physical support for said portable monitor when it is mounted on said docking station platform;
    (b) means for continuously receiving from the portable monitor in real-time patient physiological data received by the portable monitor when the portable monitor is coupled to the docking station platform; and
    (c) means for continuously transferring the received patient physiological data to the interface connection of the communications network when the portable monitor is coupled to the docking station platform, wherein said portable monitor continuously receives, processes and displays said patient physiological data while said portable monitor is being connected to and disconnected from the docking station platform, said connecting and disconnecting being accomplished without handling any individual cables or connectors.

2. A docking station platform in accordance with claim 1, further comprising means for transferring the patient data to a computer workstation by way of the communications network when the portable monitor is coupled to the docking station platform.

3. A docking station platform in accordance with claim 1, further comprising means for providing power from the docking station to the portable monitor when the portable monitor is coupled to the docking station platform.

4. A docking station platform in accordance with claim 2, in which the mounting means include:

at least one latch which secures the portable monitor to the docking station platform, preventing vertical motion between the docking station platform and the portable monitor while the portable monitor is coupled to the docking station platform; and
    at least one vertical pin which prevents horizontal motion between the portable monitor and the docking station platform while the portable monitor is coupled to the docking station platform.

5. A docking station platform in accordance with claim 2, in which the mounting means include:

at least one latch which prevents the portable monitor from being lifted off of the docking station platform while the portable monitor is coupled to the docking station platform; and
    a vertically mounted electrical connector which prevents sideways motion between the portable monitor and the docking station platform while the portable monitor is coupled to the docking station platform.

6. A docking station platform in accordance with claim 1, further comprising:

a plurality of serial ports which receive input signals from a respective plurality of input devices;
    means for coupling the serial ports to the portable monitor when the portable monitor is coupled to the docking station platform and for transmitting the input signals to the portable monitor.

7. A docking station platform in accordance with claim 1, wherein the portable monitor has a battery and a battery charger, and the docking station platform includes means for causing the battery charger to charge the battery when the portable monitor is coupled to the docking station platform.

8. A docking station platform in accordance with claim 7, wherein the portable monitor has means for detachably mounting the battery to the portable monitor, and said docking station platform includes:

a power supply and network (PSN) box, comprising:
        means for electrically coupling the PSN box to the portable monitor, and
        means for attaching the PSN box to the battery mounting means of the portable monitor when the battery is not mounted on the battery mounting means.

9. A docking station platform in accordance with claim 1, further comprising:

means for receiving an alarm signal from the portable monitor when the portable monitor is coupled to the docking station platform; and means responsive to the alarm signal receiving means for transmitting an alarm activation signal to an alarm device.

10. A docking station platform in accordance with claim 1 in which a plurality of input devices are coupled to the communications network, the docking station platform further comprising means for transferring input signals from the communications network to the portable monitor when the portable monitor is coupled to the docking station platform.

11. A docking station platform in accordance with claim 10, wherein the plurality of input devices includes a voice recognition device.

12. A docking station platform in accordance with claim 10, wherein the plurality of input devices includes a bar code reader.

13. A docking station platform in accordance with claim 10, wherein the plurality of input devices includes a remote control device which controls operation of the portable monitor.

14. A docking station platform in accordance with claim 10, wherein the plurality of input devices includes a keyboard.

15. A docking station platform in accordance with claim 1 in which a plurality of output devices are coupled to the communications network, the docking station platform further comprising means for transferring output signals from the portable monitor to the communications network when the portable monitor is coupled to the docking station platform.

16. A docking station platform in accordance with claim 15, wherein the plurality of output devices includes a label printer.

17. A docking station platform in accordance with claim 1, further comprising:
    a demultiplexer which separates the patient data received from the portable monitor into a plurality of output signals;
    means for converting the plurality of output signals into a plurality of analog signals; and
    means for transmitting the plurality of analog signals to a plurality of analog output devices.

18. A docking station platform in accordance with claim 1, further comprising means for generating and transmitting a synchronization signal to a defibrillator.

19. A docking station platform in accordance with claim 1, further comprising means for attaching the docking station to an intravenous pole.

20. A docking station platform in accordance with claim 1, further comprising means for attaching the docking station to the patient's bed.

21. A docking station platform in accordance with claim 1, further comprising means for transferring the patient data between the portable monitor and a plurality of remote stations by way of the communications network when the portable monitor is coupled to the docking station platform.

22. A docking station platform in accordance with claim 1, further including:
    a power supply and network (PSN) box, comprising:
    (1) attaching means for attaching the portable monitor to the PSN box,
    (2) means for receiving patient data at the PSN box from the portable monitor directly when the portable monitor is attached to the PSN box, and means for receiving patient data at the PSN box from the portable monitor by way of the docking station platform platform when the portable monitor is mounted on the docking station platform, and
    (3) means for transferring the received patient data to the communications network.

23. A docking station platform in accordance with claim 22, further comprising:
    means for providing power from the PSN box to the portable monitor by way of the docking station platform when the portable monitor is mounted on the docking station platform platform; and
    means for providing power from the PSN box to the portable monitor directly when the portable monitor is attached to the PSN box.

24. A docking station platform in accordance with claim 22, wherein the attaching means include means for electrically coupling the portable monitor and the PSN box.

25. A docking station platform in accordance with claim 22, wherein the portable monitor has a battery and means for mounting the battery on the portable monitor, and
    wherein the attaching means of the PSN box include means for attaching the PSN box to the battery mounting means of the portable monitor when the battery is not mounted on the battery mounting means.

26. A system for acquiring a continuous history of medical data from a plurality of sensors attached to a patient, adapted for use in at least first and second patient monitoring areas and during transport therebetween, each of said areas including at a relatively fixed location an interface for a patient data communications network, the system comprising:
    a portable monitor adapted for being battery powered and coupled to the plurality of sensors, said monitor including means for continuously receiving, processing and displaying in real-time, patient physiological data signals provided from the plurality of sensors; and
    a docking station located at said relatively fixed location in said first and second patient monitoring areas, each docking station comprising:
    first coupling means for detachably coupling the portable monitor with the docking station so as to provide an electrical connection between said portable monitor and said docking station without handling any individual cables or connectors,
    second coupling means for coupling the docking station to a power source and to the communications network, and
    transferring means for transferring in real-time patient physiological data received in real-time by said portable monitor from the portable monitor to the communications network, and power from said power source to said portable monitor, via said first and second coupling means, when said portable monitor is coupled with said docking stations,
    wherein said portable monitor continuously receives, processes and displays said patient physiological data signals while said portable monitor is being connected to and disconnected from the docking station.

27. A docking station platform in accordance with claim 23, further comprising means for transferring power from the docking station to the portable monitor when the portable monitor is coupled with the docking station.

28. A docking station in accordance with claim 26, in which the first coupling means includes:
    at least one latch which secures the portable monitor to the docking station, preventing vertical motion between the docking station and the portable monitor while the portable monitor is coupled with the docking station; and at least one vertical pin which prevents horizontal motion between the portable monitor and the docking station while the portable monitor is coupled to the docking station.

29. A docking station in accordance with claim 28, in which the first coupling means includes:

at least one latch which prevents the portable monitor from being lifted off of the docking station while the portable monitor is coupled with the docking station; and a vertically mounted electrical connector which prevents sideways motion between the portable monitor and the docking station while the portable monitor is coupled with the docking station.

30. A docking station in accordance with claim 26, wherein said communication network comprises a plurality of serial ports which receive input signals from a respective plurality of input devices; and said transferring means comprises means for coupling the serial ports to the portable monitor when the portable monitor is coupled to the docking station for transmitting the input signals to the portable monitor.

31. A docking station in accordance with claim 26, wherein the portable monitor includes a battery and a battery charger, and the docking station includes means for transferring power from said power source to said portable monitor for causing the battery charger to charge the battery when the portable monitor is coupled to the docking station.

32. A docking station in accordance with claim 31, wherein the portable monitor has means for detachably mounting the battery to the portable monitor, and said docking station includes:

a power supply and network (PSN) box, comprising:

means for electrically coupling the PSN box to the portable monitor, and means for attaching the PSN box to the battery mounting means of the portable monitor when the battery is not mounted on the battery mounting means.

33. A docking station in accordance with claim 26, wherein a plurality of output devices are coupled to the communications network, and the transferring means further comprises means for transferring output signals from the portable monitor to said output devices via the communications network when the portable monitor is coupled to the docking station.

34. A docking station in accordance with claim 23, wherein said portable monitor stores patient data when it is not coupled to said docking station, and when coupled to said docking station, transfers said stored patient data to said communication network via said first and second coupling means.

* * * * *